US006596206B2

(12) United States Patent
Lee

(10) Patent No.: US 6,596,206 B2
(45) **Date of Patent: *Jul. 22, 2003**

(54) GENERATION OF PHARMACEUTICAL AGENT PARTICLES USING FOCUSED ACOUSTIC ENERGY

(75) Inventor: David Soong-Hua Lee, Mountain View, CA (US)

(73) Assignee: Picoliter Inc., Sunnyvale, CA (US)

( * ) Notice: Subject to any disclaimer, the term of this patent is extended or adjusted under 35 U.S.C. 154(b) by 14 days.

This patent is subject to a terminal disclaimer.

(21) Appl. No.: 09/823,899

(22) Filed: Mar. 30, 2001

(65) Prior Publication Data

US 2002/0142049 A1 Oct. 3, 2002

(51) Int. Cl.[7] .................................................. B29C 9/00

(52) U.S. Cl. ....................... 264/9; 264/5; 264/7; 425/6; 425/10

(58) Field of Search ......................... 264/9, 7, 5; 425/6, 425/10

(56) References Cited

U.S. PATENT DOCUMENTS

| | | | | |
|---|---|---|---|---|
| 4,308,547 A | 12/1981 | Lovelady et al. | ....... | 346/140 R |
| 5,041,849 A | 8/1991 | Quate et al. | ............ | 346/140 R |
| 5,874,029 A | 2/1999 | Subramaniam et al. | ....... | 264/12 |
| 2002/0000681 A1 | 1/2002 | Gupta et al. | .................... | 264/9 |
| 2002/0073989 A1 | 6/2002 | Hadimioglu | ........... | 128/200.14 |
| 2002/0073990 A1 | 6/2002 | Noolandi et al. | ...... | 128/200.16 |
| 2002/0077369 A1 | 6/2002 | Noolandi et al. | ........... | 514/958 |

FOREIGN PATENT DOCUMENTS

| | | |
|---|---|---|
| EP | 0542314 | 7/1998 |
| WO | WO 00/37169 | 6/2000 |
| WO | WO 00/44468 | 8/2000 |
| WO | WO 02/00200 | 1/2002 |

OTHER PUBLICATIONS

Debenedetti et al. (1993), "Application of Supercritical Fluids for the Production of Sustained Delivery Devices," *Journal of Controlled Release* 24:27–44.

Tom et al. (1991), "Formation of Bioerodible Polymeric Microspheres and Microparticles by Rapid Expansion of Supercritical Solutions," *Biotechnol. Prog.* 7(5):403–411.

Chattopadhyay et al. (2001), "Production of Griseofulvin Nanoparticles Using Supercritical CO2 Antisolvent with Enhanced Mass Transfer," *International Journal of Pharmaceutics* 228:19–31.

Jung et al. (2001), "Particle Design Using Supercritical Fluids: Literature and Patent Survey," *Journal of Supercritical Fluids* 20:179–219.

*Primary Examiner*—Mary Lynn Theisen
(74) *Attorney, Agent, or Firm*—Dianne E. Reed; Reed & Eberle LLP

(57) ABSTRACT

A method and device for generating pharmaceutical agent particles using focused acoustic energy are provided. A solution of the pharmaceutical agent is provided in a solvent, which may be an aqueous fluid, a nonaqueous fluid, or a supercritical fluid. Focused acoustic energy is used to eject a droplet of the solution, which is then directed into or through an antisolvent that upon admixture with the solution droplet causes the pharmaceutical agent in the droplet to precipitate. In a preferred embodiment, the solvent is an aqueous or organic liquid, and the antisolvent is a supercritical fluid.

109 Claims, 1 Drawing Sheet

GENERATION OF PHARMACEUTICAL AGENT PARTICLES USING FOCUSED ACOUSTIC ENERGY

TECHNICAL FIELD

This invention relates generally to the generation of pharmaceutical agent particles, and more particularly relates to the use of focused acoustic energy in generating solid particles comprised of a pharmaceutical agent.

BACKGROUND

Rapid and efficient production of particles, particularly small and/or substantially uniform particles, is needed in a variety of industries. Among other advantages, small, substantially uniform particles possess favorable flow characteristics and exhibit little variation in interparticle behavior. In the pharmaceutical industry, for example, the particle size of a therapeutic agent can affect the dissolution rate, bioavailability and overall stability of the agent in a formulation. Precise control of the particle size of therapeutic agents is particularly important for sustained release applications, where the rate of drug release is related to the size of a particle containing the drug. In addition, pulmonary delivery of a therapeutic agent requires specifically sized particles, generally on the order of about 1 µm to about 7 µm. Particles that are too large may be deposited within the throat, while particles that are too small will be exhaled. Thus, the ability to produce small, uniform particles of a therapeutic agent is critically important in the development of particulate pharmaceutical products.

Various approaches for attaining small and uniform particles have been used. Conventional comminution techniques, e.g., crushing, grinding and milling, rely on mechanical forces to break apart relatively large particles into smaller particles. Air-jet mills and other mills, available from, for example, DT Industries, Bristol, Pa., under the tradename STOKES®, are commonly used by the pharmaceutical industry to decrease the particle size of a bulk therapeutic agent into a range suitable for pharmaceutical applications. One drawback to such mechanical comminution techniques, however, is that some therapeutic agents, particularly proteins and other therapeutic biomolecules, are damaged during the process. Another drawback of mechanical comminution is the wide distribution of particle sizes produced by these techniques. Among other problems, large variations in the size of particles limit the ability to produce sustained-release formulations and waste large amounts of therapeutic agents intended, for example, for inhalation. Although sieving a comminuted therapeutic agent through an appropriate mesh screen provides a more narrow particle size distribution, large quantities of particles not having the desired size are wasted and the potential for contamination is increased, as the therapeutic agent must contact additional surfaces.

Other techniques for producing pharmaceutical particles include conventional recrystallization methods. In such methods, the therapeutic agent is initially dissolved in a suitable solvent. In one approach, the temperature of the solution is changed so that the solubility of the solute is decreased. In another approach, a second solvent, an "antisolvent," is added so that the solubility of the solute is decreased. In both approaches, the solute precipitates or crystallizes out of the solution due to reduced solubility in the altered solution. These methods, however, often require toxic solvents, result in wet particles (that require further processing, e.g., drying), and may produce particles having variable sizes.

Supercritical fluid technology has solved some of these problems. One method for using this relatively new technology is called the rapid expansion of supercritical solutions or "RESS" method. See Tom et al. (1991) *Biotechnol. Prog.* 7(5):403–411. In the RESS method, the solute of interest, e.g., a pharmaceutical agent, is first solubilized in a supercritical fluid, i.e., a fluid at a temperature and pressure greater than its critical temperature ($T_c$) and critical pressure ($P_c$) Generally, the supercritical fluid is carbon dioxide, although other fluids are available. The solution is then rapidly passed through a nozzle that is connected to a relatively low-pressure medium. The sudden depressurization of the solution as it passes into the relatively low-pressure medium causes the supercritical fluid to expand, i.e., the density of the supercritical fluid decreases, reducing the ability of the supercritical fluid to solubilize the therapeutic agent. As a direct consequence of the reduced solubility, a supersaturated solution develops, which, in turn, causes the solute agent to precipitate or crystallize out in very small particles.

A variation of this idea is to prepare a solution of a therapeutic drug in a conventional solvent, and then spray the solution through a nozzle into a supercritical fluid that acts as an anti-solvent. When the two fluids make contact, a rapid volume expansion occurs, reducing solvent density and solvent capacity, in turn increasing supersaturation, solute nucleation and particle formulation. This method is commonly referred to as gas anti-solvent recrystallization or "GAS." See, for example, Debenedetti et al. (1993) *J. Control. Release* 24:27–44 and PCT WO 00/37169 to Merrifield. This process has been applied to various proteins to produce particle sizes of about 5 µm. See European Patent No. 0 542 314.

Although use of supercritical fluid technology offers the capability of producing relatively small particles of uniform size, it is not without drawbacks. One problem associated with these supercritical methods is the reliance on nozzles and tubes for delivering the solutions. Nozzles are known to wear down over time, altering the geometry of the equipment and affecting the size of the droplets formed. In addition, nozzles may become blocked during use, when, for example, particles agglomerate upon rapid expansion within the nozzle bore. In addition, nozzles and associated components require cleaning and may contaminate solutions when not properly maintained.

Furthermore, the droplet sizes of the solutions (both supercritical and conventional solutions) produced by methods relying on nozzles are relatively varied. As a result there will be a large variance of the surface tension between droplets of different sizes. At the sizes required for supercritical methods, the differences in surface tension between droplets causes large variations in crystallization kinetics and growth. These differences result in differently sized particles. Although U.S. Pat. No. 5,874,029 to Subramaniam et al. discusses methods for producing small-sized droplets using nozzles, the methods still suffer from the inability to effectively and consistently produce droplets of uniform size.

Thus, there is a need in the art for an improved particle formation technique wherein particle formation is highly reproducible, controllable and predictable, and substantially uniform particle size can be achieved. An ideal method would minimize or eliminate contact of the particle-forming fluid(s) with surfaces of process equipment or contaminants adsorbed thereon. The present invention addresses the aforementioned need in the art by using focused acoustic energy to eject particle-forming droplets from a pharmaceutical agent solution.

SUMMARY OF THE INVENTION

Accordingly, it is a primary object of the invention to address the aforementioned need in the art by providing a novel method and device for generating pharmaceutical agent particles using focused acoustic ejection technology.

Additional objects, advantages and novel features of the invention will be set forth in part in the description which follows, and in part will become apparent to those skilled in the art upon examination of the following, or may be learned by practice of the invention.

In one aspect, then, the invention provides a method and device for generating solid particles of pharmaceutical agents using focused acoustic energy. A solution of the pharmaceutical agent is provided in a solvent, which may be an aqueous fluid, a nonaqueous fluid, or a supercritical fluid. Focused acoustic energy is used to eject a droplet of the solution, which is then directed into or through an antisolvent that upon admixture with the solution droplet causes the pharmaceutical agent in the droplet to precipitate. The solid particle that results is then collected. In a preferred embodiment, the solvent is an aqueous or organic liquid, and the antisolvent is a supercritical fluid. It will be appreciated that the pharmaceutical agent must be less soluble in the antisolvent than in the solvent, and substantially inert in both the solvent and antisolvent.

Generally, the solution and the antisolvent will both be present in the reservoir, with the reservoir being covered or otherwise enclosed so as to provide the "contained space." The particles resulting from the ejected droplets are collected on a surface within the contained space, typically on a surface within the reservoir enclosure.

With supercritical antisolvents, expansion of the solution droplet upon ejection into a lower pressure supercritical medium causes rapid depressurization of the droplet, supersaturation thereof, and precipitation of virtually contaminant-free particles, ideally in crystalline form.

The method is advantageous in a number of respects. For example, the method:

- can be used to prepare very small particles, on the order of microns or even nanometers in diameter;
- gives rise to particles of substantially uniform size, i.e., having a narrow particle size distribution;
- can be used to prepare different crystal structures of a single molecular entity (i.e., by selection of a proper solvent and/or solvent-cosolvent combination);
- is highly reproducible, controllable and predictable;
- can be readily scaled up, but is also quite effective with very small quantities of both pharmaceutical agents and fluids, making it ideal for manufacturing particles of rare and/or expensive drugs;
- is a single-step process, in contrast to the many multi-step processes of the prior art; and
- is suitable for use with a wide range of pharmaceutical agents and excipients.

In another aspect, the invention provides a device for carrying out the aforementioned method. The device comprises: a reservoir containing a solution of the pharmaceutical agent in a solvent; an antisolvent in a contained space in fluid communication with the solution in the reservoir such that droplets ejected from the solution are directed into the antisolvent; an acoustic ejector comprising an acoustic radiation generator for generating acoustic radiation and a focusing means for focusing the acoustic radiation at a focal point within the solution in the reservoir so as to eject a droplet therefrom; and, optionally, a means for positioning the ejector in acoustic coupling relationship to the reservoir.

DETAILED DESCRIPTION OF THE INVENTION

Figure 1A:
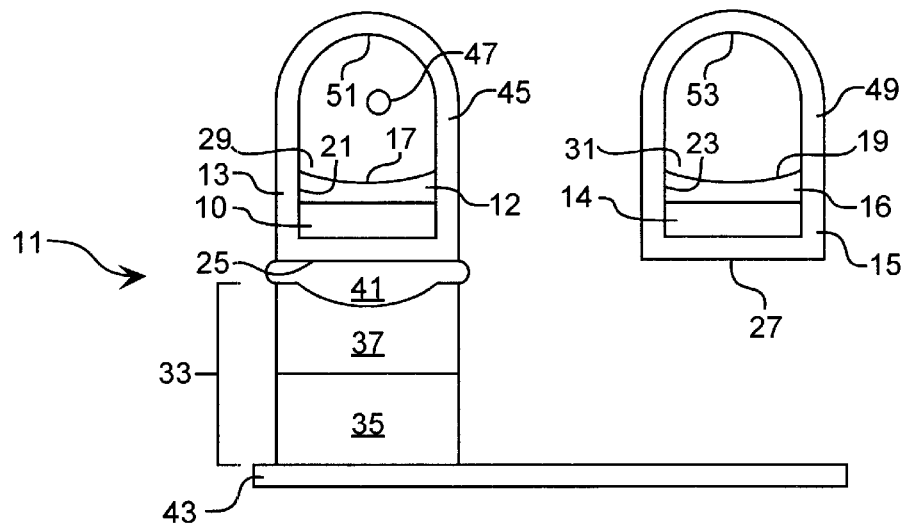
FIGS. 1A and 1B, collectively referred to as FIG. 1, schematically illustrate in simplified cross-sectional view a focused acoustic energy device useful in conjunction with preparing pharmaceutical agent particles according to the method of the invention.

Before describing the present invention in detail, it is to be understood that unless otherwise indicated this invention is not limited to specific pharmaceutical agents, fluids, acoustic ejection devices, or the like, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, the term "a solvent" is intended to mean a single solvent or a mixture of a solvent with one or more cosolvents, "a pharmaceutical agent" refers to a single pharmaceutical agent as well as to a mixture of different pharmaceutical agent, "an antisolvent" includes one antisolvent or a mixture of different antisolvents, "a reservoir" is intended to mean one or more reservoirs, and the like.

In describing and claiming the present invention, the following terminology will be used in accordance with the definitions set out below.

The terms "acoustic coupling" and "acoustically coupled" used herein refer to a state wherein a first entity is placed in direct or indirect contact with another entity so as to allow acoustic radiation to be transferred between the objects without substantial loss of acoustic energy. When two entities are indirectly acoustically coupled, an "acoustic coupling medium" is needed to provide an intermediary through which acoustic radiation may be transmitted. Thus, an ejector may be acoustically coupled to a fluid, e.g., by immersing the ejector in the fluid or by interposing an acoustic coupling medium between the ejector and the fluid to transfer acoustic radiation generated by the ejector through the acoustic coupling medium and into the fluid.

The term "fluid" as used herein refers to matter that is nonsolid or at least partially gaseous and/or liquid. A fluid may contain a solid that is minimally, partially or fully solvated, dispersed or suspended. Examples of fluids include, without limitation, aqueous liquids (including water per se and buffered water), nonaqueous liquids such as organic solvents and lipidic liquids, supercritical fluids, gases, and the like.

The term "supercritical fluid" refers to a fluid at or above both its critical pressure $P_c$ and critical temperature $T_c$. The molar volume and solubilizing capacity of a supercritical fluid can be substantially altered by varying the temperature and/or pressure of the fluid. Fluids that are slightly below their actual critical temperature and pressure can also exhibit such characteristics, and the term "supercritical fluid" is intended to encompass such fluids as well.

The term "solvent" refers to a fluid that is capable of at least partially dissolving a solute of interest.

The term "antisolvent" refers to a fluid that when mixed with a solvent in which a solute is dissolved, reduces the capacity of the solvent to dissolve the solute. Thus, when an antisolvent is admixed with a solution of a solute in a solvent, the solubility of the solute can be reduced to the point at which it precipitates out of solution. Gases, and particularly compressed gases, can act as antisolvents, although the preferred antisolvents herein are in a supercritical fluid state. The antisolvent must be sufficiently miscible with the solvent that solute precipitation does in fact result. It will be appreciated that miscibility can be controlled by varying one or more parameters within the solvent/antisolvent system, e.g., the solvent and antisolvent system may be maintained at a sufficiently low temperature so that the two fluids are not particularly miscible (for storage, for example), and the temperature may then be raised so that the two fluids are miscible and particle formation can occur.

The term "focusing means" as used herein refers to a device that causes acoustic waves to converge at a focal point by an action analogous to that of an optical lens. A focusing means may be as simple as a solid member having a curved surface, or it may include complex structures such as those found in Fresnel lenses, which employ diffraction in order to direct acoustic radiation.

The terms "particle" and "solid particle" are used interchangeably herein to refer to solid particles or particles that include solid matter. Generally, the average size of the particles prepared using the method of the invention is in the range of approximately 0.1 nm to about 5 µm in diameter, more typically in the range of approximately 5 nm to about 2.5 µm. A "droplet" is distinguishable from a particle in that droplets are nonsolid.

The terms "pharmaceutical agent," "active agent" and "drug" are used interchangeably herein to refer to a chemical material or compound which, when administered to an organism (human or animal) induces a desired pharmacological effect, including therapeutic effects, prophylactic effects, and diagnostic effects.

By "pharmaceutically acceptable carrier" is meant a material or materials that are suitable for drug administration and not biologically or otherwise undesirable, i.e., that may be administered to an individual along with an active agent without causing any undesirable biological effects or interacting in a deleterious manner with any of the other components of the pharmaceutical formulation in which it is contained.

Similarly, a "pharmacologically acceptable" salt, ester or other derivative of an active agent as provided herein is a salt, ester or other derivative that is not biologically or otherwise undesirable.

The term "reservoir" as used herein refers a receptacle or chamber for holding or containing a fluid. Thus, a fluid in a reservoir necessarily has a free surface, i.e., a surface that allows a droplet to be ejected therefrom.

"Optional" or "optionally" means that the subsequently described circumstance may or may not occur, so that the description includes instances where the circumstance occurs and instances where it does not.

The pharmaceutical agent may be any known or hereafter discovered pharmacologically active agent, and may be a compound that occurs in nature, a chemically modified naturally occurring compound, or a compound that is chemically synthesized. The agent will typically be chosen from the generally recognized classes of pharmacologically active agents, including, but not necessarily limited to, the following: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; psychostimulants; sedatives; steroids; sympathomimetics; tranquilizers; and vasodilators including general coronary, peripheral and cerebral.

The pharmaceutical agent may also be a biomolecule, e.g., a molecular moiety selected from the group consisting of DNA, RNA, antisense oligonucleotides, peptidyl drugs, i.e., peptides, polypeptides and proteins (including fluorescent proteins), ribosomes and enzyme cofactors such as biotin. Biomolecules (as well as other agents) may be radioactively tagged or otherwise labeled for diagnostic purposes, as will be discussed in further detail below.

Suitable pharmacologically active peptides will generally although not necessarily have a molecular weight of at least 300 Da, and preferably at least 800 Da. Examples of such peptides which may be substantially stable in the extended release formulations over the intended period of release, and which may therefore be used in the compositions of this invention, are oxytocin, vasopressin, adrenocorticotropic hormone (ACTH), epidermal growth factor (EGF), prolactin, luteinizing hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumour necrosis factor, colony stimulating factors, motilin, bombesin, dinorphin, neurotensin, cerulein, bradykinin, urokinase, kallikrein, substance P analogues and antagonists, angiotensin II, nerve growth factor, blood coagulation factors VII and IX, lysozyme chloride, renin, bradykinin, tyrocidin, gramicidines, growth hormones, melanocyte stimulating hormone, thyroid hormone releasing hormone, thyroid stimulating hormone, parathyroid hormone, pancreozymin, cholecystokinin, human placental lactogen, human chorionic gonadotropin, protein synthesis stimulating peptide, gastric inhibitory peptide, vasoactive intestinal peptide, platelet derived growth factor, growth hormone releasing factor, bone morphogenic protein, and synthetic analogues and modifications and pharmacologically active fragments thereof. Peptidyl drugs also include synthetic analogs of LHRH, e.g., buserelin, deslorelin, fertirelin, goserelin, histrelin, leuprolide (leuprorelin), lutrelin, nafarelin, tryptorelin, and pharmacologically active salts thereof.

Those skilled in the art will recognize that since the invention is used in the manufacture of particles and powders, the primary pharmaceutical agent candidates will be those that are suitable for administration of particulate dosage forms, e.g., using inhalation therapy and, for example, a dry powder inhaler. Delivery of pharmaceutical particles via the respiratory system is of increasing interest in the pharmaceutical field, particularly for those active agents that are problematic when administered orally, e.g., cause gastrointestinal distress and/or have variable rates of absorption and metabolism.

Pharmaceutical agents that are known candidates for administration using dry powder inhalation therapy include the following: peptidyl drugs, as described above; analgesics, e.g., codeine, dihydromorphine, ergotamine, fentanyl and morphine; anginal preparations, e.g., diltiazem; anti-allergy agents, e.g., cromoglycates such as cromolyn sodium, ketotifen or nedocromil; antihistamines, e.g., methapyrilene; and respiratory drugs, i.e., pharmaceutical agents that are used in the treatment of respiratory diseases such as asthma, bronchitis, emphysema and cystic fibrosis. Respiratory drugs include: anti-inflammatory corticosteroids, e.g., flunisolide, flunisolide hemihydrate, budesonide, beclomethasone, beclomethasone monopropionate, beclomethasone dipropionate, dexamethasone, dexamethasone sodium phosphate, fluticasone, and triamcinolone acetonide; antitussives, e.g., noscapine; bronchodilators, including $\beta_2$ adrenergic agonists, anticholinergic agents, and xanthine derivatives, e.g. albuterol, bitolterol, clenbuterol, ephedrine, adrenaline, fenoterol, formoterol, isoprenaline, isoproterenol, isoproterenol sulfate, levalbuterol (i.e., homochiral (R)-albuterol), metaproterenol, metaproterenol sulfate, phenylephrine, pirbuterol, pirbuterol acetate, procaterol, reproterol, rimiterol, salmeterol, salmeterol xinotoate, terbutaline, and terbutaline sulfate; anticholinergics, e.g., ipratropium bromide, atropine and oxitropium; and xanthines, e.g. aminophylline, choline theophyllinate, lysine theophyllinate or theophylline.

The pharmaceutical agent may also be a diagnostic agent, insofar as pulmonary administration of fine particles for diagnosis is well known. These diagnostic particles include MRI contrast agents and radio-labeled compounds, known to be useful for diagnosis of pulmonary abnormalities, including abnormalities of function and structure, blockages, tumors, and the like. Examples of such diagnostic particles include, but are not limited to, $Na_2Fe$-diethylenetriamine pentaacetic acid (DTPA), $Na_2Cr(DTPA)$, $Na_2Ge(DTPA)$, gadolinium (III) contrast agents, radioactive rhenium-containing or phosphorus-containing salts, 2,2,6,6,-tetramethyl-1-piperidinoxyl (TEMPO) spin-label agents and other contrast aids.

It will be appreciated by those skilled in the art of pharmaceutical formulation and drug delivery that particulate dosage forms such as those prepared herein will typically include components other than the active agent. In order to incorporate these additional components, they are added to the agent-containing solvent prior to droplet ejection into the antisolvent fluid. For example, a dry powder composition for pulmonary administration will typically include a carrier such as a mono-, di- or polysaccharide, including dextrose (anhydrous and the monohydrate; also referred to as glucose and glucose monohydrate), lactitol, lactose, maltitol, maltose, sucrose, fructose, galactose, mannitol, D-mannose, melezitose, myoinositol, palatinite, raffinose, sorbitol, sorbose, stachyose, trehalose, xylitol, cellulosic polymers such as hydroxypropyl methylcellulose, cyclodextrins such as 2-hydroxypropyl-β-cyclodextrin, or the like, and the selected carrier would be dissolved in the solvent along with the pharmaceutical agent prior to droplet ejection and particle formation.

Other additives commonly included in particulate pharmaceuticals include diluents, stabilizers, surfactants, lubricants, etc., and may be incorporated into the pharmaceutical particles prepared herein in an analogous manner.

For controlled release particles, from which the drug releases gradually in a controlled manner, a biodegradable polymer may be incorporated into the solid particles prepared according to the invention as described above for carriers and other additives. The biodegradable polymer may be used in any convenient amount relative to the pharmaceutical agent, and the weight ratio of the biodegradable polymer to the pharmaceutical agent can vary from about 0.1 to 1 to about 100,000 to 1 depending upon the application. Most controlled release applications, however, will involve a weight ratio of from about 10 to 1 to about 100 to 1. Any biodegradable polymer may be used that may be co-dissolved in the organic solvent along with the pharmaceutical agent. Examples of such biodegradable polymers include those prepared by polymerization of at least one of the following: an α-hydroxycarboxylic acid; a cyclic diester of an α-hydroxycarboxylic acid; a dioxanone; a lactone; a cyclic carbonate; a cyclic oxalate; an epoxide; a glycol; and an anhydride. Preferred biodegradable polymers are poly (ortho esters), poly (ϵ-caprolactone), and poly (lactide-co-glycolide). The biodegradable polymers may be a homopolymer or a copolymer of two or more different monomers. Preferred homopolymers include poly(lactic acid), polylactide, poly(glycolic acid), polyglycolide and poly(ethylene glycol).

Depending on the hydrophilicity of the pharmaceutical agent, suitable solvents for the pharmaceutical agent will be either hydrophilic or lipophilic. Hydrophilic agents will of course dissolve in aqueous solvents and other hydrophilic solvents, while hydrophobic agents will dissolve in lipophilic, nonaqueous solvents, the latter including, for example, many organic solvents and lipidic fluids. Supercritical fluids may also serve as solvents for the pharmaceutical agent, but will generally be used as antisolvents, i.e., as precipitating fluids. The solution of the pharmaceutical agent in the solvent will generally although not necessarily be saturated, such that supersaturation results when a solution droplet contacts and admixes with the antisolvent.

Aqueous solvents comprise water, and may additionally include other components that are soluble or miscible in the water, which components may be useful or desired for particular applications. Thus, aqueous solvents herein may include, but not limited to, water, a water-ethanol or water-isopropanol admixture, ammonia water, a buffered aqueous medium, acidified water, basified water, and the like.

Examples of organic solvents include, without limitation: hydrocarbons, including aliphatic alkanes such as hexane, heptane, decalin, octane, etc., cyclic alkanes such as cyclohexane, and aromatic hydrocarbons such as benzene, cumene, pyridine, pseudocumene, cymene, styrene, toluene, xylenes, tetrahydronaphthalene and mesitylene; halogenated compounds such as carbon tetrachloride and chlorinated, fluorinated and brominated hydrocarbons such as chloroform, bromoform, methyl chloroform, chlorobenzene, o-dichlorobenzene, chloroethane, 1,1-dichloroethane, 1,2-dichloroethane, tetrachloroethane, epichlorohydrin, trichloroethylene and tetrachloroethylene; ethers such as diethyl ether, diisopropyl ether, diisobutyl ether, diglyme, 1,4-dioxane, 1,3-dioxolane, dimethoxymethane, furan and tetrahydrofuran; aldehydes such as methyl formate, ethyl formate and furfural; ketones such as acetone, diisobutyl ketone, cyclohexanone, methyl ethyl ketone, N-methyl-2-pyrrolidone and isophorone; amides such as dimethyl formamide and dimethyl acetamide; alcohols such as ethanol, isopropanol, n-propanol, t-butyl alcohol, cyclohexanol, 1-hexanol, 1-octanol and trifluoroethanol; polyhydric alcohols such as 1,3-propanediol, glycerol, ethylene glycol, propylene glycol, and low molecular weight (typically less than 400) polyethylene glycol; amines, including cyclic amines such as pyridine, piperidine, 2-methylpyridine, morpholine, etc., and mono-, di- and tri-substituted amines such as trimethylamine, dimethylamine, methylamine, triethylamine, diethylamine, ethylamine, n-butylamine, t-butylamine, triethanolamine, diethanolamine and ethanolamine, and amine-substituted hydrocarbons such as ethylene diamine, diethylene triamine; carboxylic acids such as acetic acid, trifluoroacetic acid and formic acid; esters such as ethyl acetate, isopentyl acetate, propylacetate, etc.; lactams such as caprolactam; nitriles such as acetonitrile, propane nitrile and adiponitrile; organic nitrates such as nitrobenzene, nitroethane and nitromethane; and sulfides such as carbon disulfide.

The solvent may also be a lipidic material including, but not limited to, the following: phospholipids such as phosphorylated diacyl glycerides, and particularly phospholipids selected from the group consisting of diacyl phosphatidylcholines, diacyl phosphatidylethanolamines, diacyl phosphatidylserines, diacyl phosphatidylinositols, diacyl phosphatidylglycerols, diacyl phosphatidic acids, and mixtures thereof, wherein each acyl group contains about 10 to about 22 carbon atoms and is saturated or unsaturated; fatty acids such as isovaleric acid, valeric acid, caproic acid, enanthic acid, caprylic acid, pelargonic acid, capric acid, lauric acid, myristic acid, palmitic acid, stearic acid, arachidic acid, behenic acid, lignoceric acid, oleic acid, linoleic acid, linolenic acid, and arachidonic acid; lower fatty acid esters comprising esters of the foregoing fatty acids, wherein the carboxylic acid group of the fatty acid is replaced with an ester moiety —(CO)—OR wherein R is a $C_1$–$C_3$ alkyl moiety optionally substituted with one or two hydroxyl groups; fatty alcohols corresponding to the aforementioned fatty acids, wherein the carboxylic acid group of the fatty acid is replaced by a —$CH_2OH$ group; glycolipids such as cerebroside and gangliosides; oils, including animal oils such as cod liver oil and, menhaden oil, and vegetable oils such as babassu oil, castor oil, corn oil, cotton seed oil, linseed oil, mustard oil, olive oil, palm oil, palm kernel oil, peanut oil, poppyseed oil, rapeseed oil, safflower oil, sesame oil, soybean oil, sunflower seed oil, tung oil or wheat germ oil; and waxes, i.e., higher fatty acid esters, including animal waxes such as beeswax and shellac, mineral waxes such as montan, petroleum waxes such as microcrystalline wax and paraffin, and vegetable waxes such as carnauba wax.

In a preferred embodiment, a supercritical fluid is used as the antisolvent, or precipitating fluid, effective to cause the pharmaceutical agent to precipitate upon admixture with the pharmaceutical agent-solvent solution. Although it is preferable that the agent be insoluble in the antisolvent, it is sufficient for the purpose of the present invention that the agent be less soluble in the antisolvent than in the solvent. Thus, it is possible that the antisolvent fluid may be capable of dissolving some amount of the pharmaceutical agent, although in a preferred embodiment, the antisolvent fluid is substantially incapable of dissolving a significant portion of the pharmaceutical agent. Also, the antisolvent fluid is at least partially miscible with the organic solvent such that the antisolvent fluid is capable of penetrating into the pharmaceutical agent-solvent solution sufficiently to cause the desired precipitation of the pharmaceutical agent. The antisolvent fluid may comprise any suitable fluid for near critical or supercritical processing. These fluids include, for example, carbon dioxide, water, ammonia, nitrogen, nitrous oxide, methane, ethane, ethylene, propane, butane, n-pentane, benzene, methanol, ethanol, isopropanol, isobutanol, halocarbons (including monofluoromethane, trifluoromethane, chlorotrifluoromethane, monofluoromethane, hexafluoroethane 1,1-difluoroethylene and 1,2-difluoroethylene), toluene, pyridine, cyclohexane, m-cresol, decalin, cyclohexanol, o-xylene, tetralin, aniline, acetylene, chlorotrifluorosilane, xenon, sulfur hexafluoride, propane, and others. Cosolvents or other modifiers may be added to the supercritical fluid to change its intrinsic properties in or around the critical point. Suitable cosolvents and modifiers are known in the art and include, for example, methanol, ethanol, isopropanol and acetone.

For many pharmaceutical agents, it is desirable to use an antisolvent fluid that permits processing at relatively mild temperatures. This is particularly important for processing peptidyl drugs, which are susceptible to a loss of biological activity when subjected either to very low temperatures or to very high temperatures. For processing of proteins and polypeptides, then, the antisolvent fluid should preferably have a critical temperature of from about 0° C. to about 50° C. Included in this category of antisolvent fluids are carbon dioxide, nitrogen, nitrous oxide, ethane, ethylene, chlorotrifluoromethane, monofluoromethane, acetylene, 1,1-difluoroethylene, hexafluoroethane, chlorotrifluorosilane, and xenon. A particularly preferred antisolvent fluid is carbon dioxide because it is readily available, non-toxic (it has "GRAS," or "generally regarded as safe," status), non-flammable, relatively low cost, has low chemical reactivity, and has a critical temperature of 31.3° C. and a critical pressure of 72.9 atm (1072 psi), which permits processing under relatively mild conditions. Another preferred supercritical fluid is nitrogen.

After preparation, the drug-containing particles are packaged, as is or in dosage forms, preferably dosage forms containing a unit dose of the active agent. For pulmonary administration, the powders may be incorporated into a suitable inhaler. For oral delivery pharmaceutical powders may be dissolved in water prior to administration, although capsules are preferred for oral administration. Suitable capsule materials may be either hard or soft, and as will be appreciated by those skilled in the art, typically comprise a tasteless, easily administered and water soluble compound such as gelatin, starch or a cellulosic material. See *Remington: The Science and Practice of Pharmacy,* Nineteenth Edition (Easton, Pa.: Mack Publishing Co., 1995), which describes materials and methods for preparing encapsulated pharmaceuticals. Each capsule will typically contain a therapeutically effective dose of the active agent. Alternatively, the dosage forms may contain less than a therapeutically effective dose in which case administration of two or more dosage forms would be required to achieve the therapeutically effective dose.

It will also be appreciated by those of skill in the art that particulate pharmaceutical preparations may be manufactured in other ways, and administered using any convenient method. For example, douche powders are typically dissolved in water prior to use as antiseptics or as cleansing agents for a body cavity, typically for vaginal administration, but also for nasal, otic or ophthalmic use. The powders may also be used as "dusting" powders, i.e., locally applied preparations that are intended to have no systemic action, used, for example, as lubricants, protectives, absorbents, antiseptics, antipruritics, antibromhidrosis agents, astringens and antiperspirants. Powders may also be introduced into the body directly, without a carrier liquid, as "insufflations," in which case an insufflator (powder blower) or pressure aerosol device is used to introduce the powder into body cavities such as the ears, nose and throat. It may be necessary to dilute the pharmaceutical powder with an inactive solid carrier, also in powder form, to produce what is commonly called a "trituration."

In preparing solid particles according to the invention, focused acoustic energy is used substantially as described in detail in co-pending patent applications U.S. Ser. No. 09/669,996 ("Acoustic Ejection of Fluids From a Plurality of Reservoirs"), inventors Ellson and Foote, and U.S. Ser. No. 09/669,194 ("Method and Device for Generating Droplets of Immiscible Fluids"), inventors Ellson, Mutz and Foote, both filed on Sep. 25, 2000 and assigned to Picoliter Inc. (Sunnyvale, Calif.). FIG. 1 illustrates a focused acoustic ejection device that can be used in accordance with the foregoing method. The device is shown in simplified cross-sectional view, wherein, as with all figures referenced herein, like parts are referenced by like numerals, the figure is not necessarily to scale, and certain dimensions may be exaggerated for clarity of presentation. The device 11 may include a single reservoir, two reservoirs, or a plurality of reservoirs. For simplicity, the device is illustrated as containing two reservoirs, with a first reservoir indicated at 13 and a second reservoir indicated at 15. Each reservoir contains a solution of the pharmaceutical agent provided in a solvent, with the antisolvent in a contained space generally above and in fluid communication with the solution in the reservoir such that droplets ejected from the solution are directed into the antisolvent. The solvent may comprise a mixture of solvents, and the antisolvent, similarly, may comprise a mixture of antisolvents. Reservoirs containing both the solution and the antisolvent are illustrated in the figure, with reservoir 13 containing the pharmaceutical agent—solvent solution as a lower fluid 10 and the antisolvent as an upper fluid 12, and, analogously, reservoir 15 containing the pharmaceutical agent solution as a lower fluid 14 and the antisolvent as an upper fluid 16. Generally, with liquid antisolvents, the upper fluid layer comprised of the antisolvent will have a thickness (i.e., height) that is less than about 10% of the thickness of the lower fluid layer comprised of the solvent, typically in the range of about 0.1% to 5% of the thickness of the lower fluid. It must be emphasized, however, that the two-phase system is illustrated and described merely for simplicity, and each reservoir may contain three or more fluids, and the invention is not limited in this regard. For example, a third fluid may be incorporated so as to physically segregate the solvent and antisolvent. Alternatively, the solvent and antisolvent may be maintained in a substantially segregated state by maintaining the solvent, the antisolvent, or both, at a predetermined temperature and pressure.

With liquid antisolvents, upper fluid layers 12 and 16 will have fluid surfaces respectively indicated at 17 and 19. As shown, the reservoirs are of substantially identical construction so as to be substantially acoustically indistinguishable, but identical construction is not a requirement. The reservoirs are shown as separate removable components but may, if desired, be fixed within a plate or other substrate. For example, the reservoirs may be individual wells in a well plate. Each of the reservoirs 13 and 15 is preferably axially symmetric as shown, having vertical walls 21 and 23 extending upward from circular reservoir bases 25 and 27 and terminating at openings 29 and 31, respectively, although other reservoir shapes may be used. The material and thickness of each reservoir base should be such that acoustic radiation may be transmitted therethrough.

The device also includes an acoustic ejector 33 comprised of an acoustic radiation generator 35 for generating acoustic radiation and a focusing means 37 for focusing the acoustic radiation at a focal point within the upper fluid layer or the lower fluid layer, but is preferably just below the interface therebetween. As shown in FIG. 1, the focusing means 37 may comprise a single solid piece having a concave surface 39 for focusing acoustic radiation, but the focusing means may be constructed in other ways as discussed below. The acoustic ejector 33 is thus adapted to generate and focus acoustic radiation so as to eject a droplet of fluid from the solution into the antisolvent when acoustically coupled to the reservoirs. The acoustic radiation generator 35 and the focusing means 37 may function as a single unit controlled by a single controller, or they may be independently controlled, depending on the desired performance of the device. Typically, single ejector designs are preferred over multiple ejector designs because accuracy of droplet velocity (i.e., both the speed and direction of the ejected droplet) and consistency in droplet size and velocity are more easily achieved with a single ejector.

As will be appreciated by those skilled in the art, any of a variety of focusing means may be employed in conjunction with the present invention. For example, one or more curved surfaces may be used to direct acoustic radiation to a focal point near a fluid surface. One such technique is described in U.S. Pat. No. 4,308,547 to Lovelady et al. Focusing means with a curved surface have been incorporated into the construction of commercially available acoustic transducers such as those manufactured by Panametrics Inc. (Waltham, Mass.). In addition, Fresnel lenses are known in the art for directing acoustic energy at a predetermined focal distance from an object plane. See, e.g., U.S. Pat. No. 5,041,849 to Quate et al. Fresnel lenses may have a radial phase profile that diffracts a substantial portion of acoustic energy into a predetermined diffraction order at diffraction angles that vary radially with respect to the lens. The diffraction angles should be selected to focus the acoustic energy within the diffraction order on a desired object plane.

There are also a number of ways to acoustically couple the ejector 33 to an individual reservoir and thus to the fluid therein. One such approach is through direct contact as is described, for example, in U.S. Pat. No. 4,308,547 to Lovelady et al., wherein a focusing means constructed from a hemispherical crystal having segmented electrodes is submerged in a liquid to be ejected. The aforementioned patent further discloses that the focusing means may be positioned at or below the surface of the liquid. However, this approach for acoustically coupling the focusing means to a fluid is undesirable when the ejector is used to eject different fluids in a plurality of containers or reservoirs, as repeated cleaning of the focusing means would be required in order to avoid cross-contamination; contamination of any sort must, of course, be avoided in the preparation of pharmaceuticals. The cleaning process would necessarily lengthen the transition time between each droplet ejection event. In addition, in such a method, fluid would adhere to the ejector as it is removed from each container, wasting material that may be costly or rare.

Thus, a preferred approach, when a multiple reservoir system is employed, is to acoustically couple the ejector to the reservoirs and reservoir fluids without contacting any portion of the ejector, e.g., the focusing means, with any of the fluids to be ejected. To this end, an ejector positioning means may be provided for positioning the ejector in controlled and repeatable acoustic coupling with each of the fluids in the reservoirs to eject droplets therefrom without submerging the ejector therein. This typically involves direct or indirect contact between the ejector and the external surface of each reservoir. When direct contact is used in order to acoustically couple the ejector to each reservoir, it is preferred that the direct contact is wholly conformal to ensure efficient acoustic energy transfer. That is, the ejector and the reservoir should have corresponding surfaces adapted for mating contact. Thus, if acoustic coupling is achieved between the ejector and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs having a specially formed inverse surface.

Optimally, acoustic coupling is achieved between the ejector and the reservoir through indirect contact, as illustrated in FIG. 1A. In the figure, an acoustic coupling medium 41 is placed between the ejector 33 and the base 25 of reservoir 13, with the ejector and reservoir located at a predetermined distance from each other. The acoustic coupling medium may be an acoustic coupling fluid, preferably an acoustically homogeneous material in conformal contact with both the acoustic focusing means 37 and each reservoir. In addition, it is important to ensure that the fluid medium is substantially free of material having different acoustic properties than the fluid medium itself. As shown, the reservoir 13 is acoustically coupled to the acoustic focusing means 37 such that an acoustic wave is generated by the acoustic radiation generator and directed by the focusing means 37 into the acoustic coupling medium 41, which then transmits the acoustic radiation into the reservoir. The acoustic ejector 33 is positionable by means of ejector positioning means 43, shown below reservoir 13, in order to achieve acoustic coupling between the ejector and the reservoir through acoustic coupling medium 41. Once the ejector, the reservoir and the substrate are in proper alignment, the acoustic radiation generator 35 is activated to produce acoustic radiation that is directed by the focusing means 37 to a focal point within solution 10 in the first reservoir. As a result, droplet 47 is ejected from the solution, into the antisolvent 12, and optionally onto a site on the underside surface 51 of the enclosure 45.

Figure 1B:
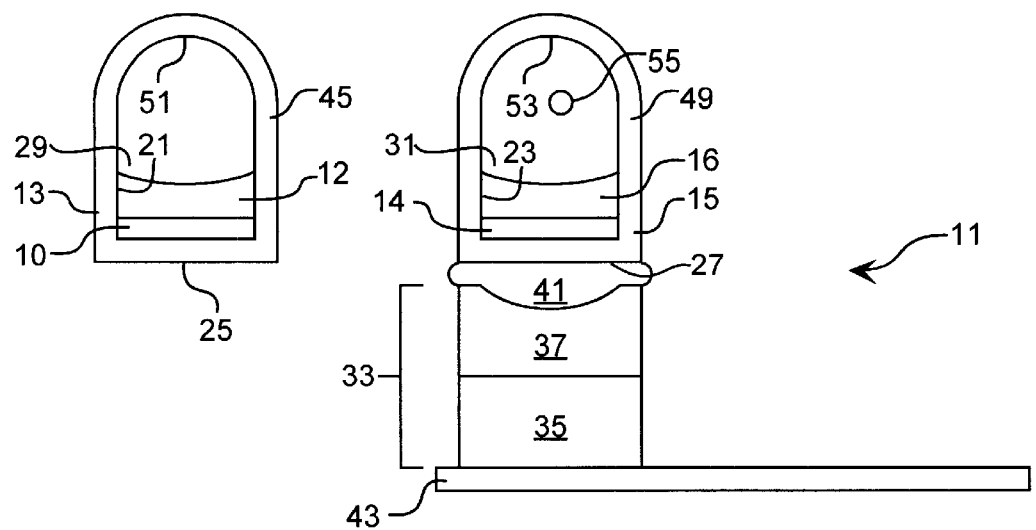

Then, as shown in FIG. 1B, the ejector 33 has been repositioned below reservoir 15 and in acoustically coupled relationship thereto by virtue of acoustic coupling medium 41. Once properly aligned as shown in FIG. 1B, the acoustic radiation generator 35 of ejector 33 is activated to produce acoustic radiation that is then directed by focusing means 37 to a focal point within the solution in reservoir 15, thereby ejecting droplet 55 into the antisolvent 16 and optionally onto the underside 53 of enclosure 49. As discussed above, a single reservoir may be used or two or more reservoirs may be used, wherein the well(s) may be removable or contained within a well plate. Similarly, a single ejector can be used, as shown in the figures, or a plurality of ejectors can be used with each ejector positioned so as to eject a droplet from a different locus within a single reservoir (if a single reservoir is used) or from each of a plurality of reservoirs. Also, unless it is intended that the ejector is to be submerged in the fluids to be ejected, the reservoirs or well plates must have acoustic transmission properties sufficient to allow acoustic radiation from the ejector to be conveyed to the surfaces of the fluids to be ejected. Typically, this involves providing reservoir or well bases that are sufficiently thin to allow acoustic radiation to travel therethrough without unacceptable dissipation.

In addition, the material used in the construction of reservoirs must be compatible with the fluids contained therein. Thus, if it is intended that the reservoirs or wells contain a particular organic solvent, polymers that dissolve or swell in that solvent would be unsuitable for use in forming the reservoirs or well plates. For water-based fluids, a number of materials are suitable for the construction of reservoirs and include, but are not limited to, ceramics such as silicon oxide and aluminum oxide, metals such as stainless steel and platinum, and polymers such as polyester and polytetrafluoroethylene. Many well plates are commercially available and may contain, for example, 96, 384 or 1536 wells per well plate. Manufactures of suitable well plates for use in the inventive device include Corning Inc. (Corning, N.Y.) and Greiner America, Inc. (Lake Mary, Fla.). However, the availability of such commercially available well plates does not preclude manufacture and use of custom-made well plates containing at least about 10,000 wells, or as many as 100,000 wells or more. In addition, for multiple reservoir systems, it is preferable that the center of each reservoir is located not more than about 1 centimeter, preferably not more than about 1 millimeter and optimally not more than about 0.5 millimeter from another reservoir center. In order to ensure the accuracy of fluid ejection, it is important to determine the location and the orientation of the fluid surface from which a droplet is to be ejected with respect to the ejector. Otherwise, ejected droplets may be improperly sized or travel in an improper trajectory. Thus, another embodiment of the invention relates to a method for determining the height of a fluid surface in a reservoir between ejection events. The method involves activating the acoustic generator to produce a detection acoustic wave that travels to the fluid surface and is reflected thereby as a reflected acoustic wave. Parameters of the reflected acoustic radiation are then analyzed in order to assess the spatial relationship between the acoustic radiation generator and the fluid surface. Such an analysis will involve the determination of the distance between the acoustic radiation generator and the fluid surface and/or the orientation of the fluid surface in relationship to the acoustic radiation generator.

More particularly, the acoustic radiation generator may activated so as to generate low energy acoustic radiation that is insufficiently energetic to eject a droplet from the fluid surface in the reservoir. This is typically done by using an extremely short pulse (on the order of tens of nanoseconds) relative to that normally required for droplet ejection (on the order of microseconds). By determining the time it takes for the acoustic radiation to be reflected by the fluid surface back to the acoustic radiation generator and then correlating that time with the speed of sound in the fluid, the distance—and thus the fluid height—may be calculated. Of course, care must be taken in order to ensure that acoustic radiation reflected by the interface between the reservoir base and the fluid is discounted. It will be appreciated by those of ordinary skill in the art of acoustic microscopy that such a method employs conventional or modified sonar techniques.

Once the analysis has been performed, an ejection acoustic wave having a focal point near the fluid surface is generated in order to eject at least one droplet of the fluid, wherein the optimum intensity and directionality of the ejection acoustic wave is determined using the aforementioned analysis optionally in combination with additional data. The "optimum" intensity and directionality are generally selected to produce droplets of consistent size and velocity. For example, the desired intensity and directionality of the ejection acoustic wave may be determined by using not only the spatial relationship assessed as above, but also geometric data associated with the reservoir, fluid property data associated with the fluid to be ejected, and/or by using historical droplet ejection data associated with the ejection sequence. In addition, the data may show the need to reposition the ejector so as to reposition the acoustic radiation generator with respect to the fluid surface, in order to ensure that the focal point of the ejection acoustic wave is near the fluid surface, where desired. For example, if analysis reveals that the acoustic radiation generator is positioned such that the ejection acoustic wave cannot be focused near the fluid surface, the acoustic radiation generator is repositioned using vertical, horizontal and/or rotational movement to allow appropriate focusing of the ejection acoustic wave.

The device may include other components that enhance performance. For example, the device may further comprise cooling means for lowering the temperature of a particle collection means (e.g., an upper surface within the contained enclosure) positioned above the reservoir. The device may also comprise a heating means for maintaining the fluid in the reservoir at a constant temperature, and which, in combination with a pressurizing means, for maintaining the antisolvent in a supercritical state. Design and construction of such temperature maintaining means and pressurizing means are known to one of ordinary skill in the art. For many biomolecular applications, it is generally desired that the fluid containing the biomolecule is kept at a constant temperature without deviating more than about 1° C. or 2° C. therefrom. In addition, for a biomolecular fluid that is particularly heat sensitive, it is preferred that the fluid be kept at a temperature that does not exceed about 10° C. above the melting point of the fluid, preferably at a temperature that does not exceed about 5° C. above the melting point of the fluid. Thus, for example, when the biomolecule-containing fluid is aqueous, it may be optimal to keep the fluid at about 4° C. during ejection.

The device of the invention enables ejection of droplets at a rate of at least about 1,000,000 droplets per minute from the same reservoir, and at a rate of at least about 100,000 drops per minute from different reservoirs. In addition, current positioning technology allows for the ejector positioning means to move from one reservoir to another quickly and in a controlled manner, thereby allowing fast and controlled ejection of different fluids. That is, current commercially available technology allows the ejector to be moved from one reservoir to another, with repeatable and controlled acoustic coupling at each reservoir, in less than about 0.1 second for high performance positioning means and in less than about 1 second for ordinary positioning means. A custom designed system will allow the ejector to be moved from one reservoir to another with repeatable and controlled acoustic coupling in less than about 0.001 second. In order to provide a custom designed system, it is important to keep in mind that there are two basic kinds of motion: pulse and continuous. Pulse motion involves the discrete steps of moving an ejector into position, emitting acoustic energy, and moving the ejector to the next position; again, using a high performance positioning means with such a method allows repeatable and controlled acoustic coupling at each reservoir in less than 0.1 second. A continuous motion design, on the other hand, moves the ejector and the reservoirs continuously, although not at the same speed, and provides for ejection during movement. Since the pulse width is very short, this type of process enables over 10 Hz reservoir transitions, and even over 1000 Hz reservoir transitions.

I claim:

1. A method for generating a solid particle containing a pharmaceutical agent, the method comprising:
   providing a reservoir containing a solution of the pharmaceutical agent in a solvent;
   providing an antisolvent in a contained space in fluid communication with the solution in the reservoir, wherein the antisolvent is selected such that the pharmaceutical agent is less soluble in the antisolvent than in the solvent; and
   applying focused acoustic energy to the reservoir so as to produce a droplet of the solution in the antisolvent in the contained space, whereby admixture of the solution droplet and the antisolvent results in the precipitation of the pharmaceutical agent, forming a solid particle.

2. The method of claim 1, wherein focused acoustic energy is applied to the reservoir at a plurality of loci so as to eject a plurality of droplets, whereby a plurality of solid particles is provided.

3. The method of claim 1, wherein the solvent is aqueous.

4. The method of claim 1, wherein the solvent is non-aqueous.

5. The method of claim 4, wherein the solvent is organic.

6. The method of claim 1, wherein the solvent is a supercritical fluid.

7. The method of claim 1, wherein the antisolvent is a supercritical fluid.

8. The method of claim 4, wherein the antisolvent is a supercritical fluid.

9. The method of claim 5, wherein the antisolvent is a supercritical fluid.

10. The method of claim 1, wherein the antisolvent is gaseous.

11. The method of claim 1, wherein the precipitation of the pharmaceutical agent comprises crystallization thereof.

12. The method of claim 1, wherein the solution and the antisolvent are both present in the reservoir.

13. The method of claim 12, wherein a third fluid is present as a segregating layer between the solution and the antisolvent.

14. The method of claim 12, wherein the solvent and antisolvent are maintained in a substantially segregated state by maintaining the solvent, the antisolvent, or both, at a predetermined temperature and pressure.

15. The method of any one of claims 7, 8, 9, 12, 13 and 14, wherein the antisolvent is selected from the group consisting of carbon dioxide, water, ammonia, nitrogen, nitrous oxide, methane, ethane, ethylene, propane, butane, n-pentane, benzene, methanol, ethanol, isopropanol, isobutanol, monofluoromethane, trifluoromethane, chlorotrifluoromethane, monofluoromethane, hexafluoroethane, 1,1-difluoroethylene, 1,2-difluoroethylene, toluene, pyridine, cyclohexane, m-cresol, decalin, cyclohexanol, o-xylene, tetralin, aniline, acetylene, chlorotrifluorosilane, xenon, sulfur hexafluoride, propane, and combinations thereof.

16. The method of claim 15, wherein the antisolvent is carbon dioxide.

17. The method of claim 1, wherein the solution droplet is ejected onto a surface of a substrate having the antisolvent thereon.

18. The method of claim 1, wherein the solution is a saturated solution.

19. The method of claim 1, wherein the pharmaceutical agent is hydrophilic, the solvent is hydrophilic, and the antisolvent is lipophilic.

20. The method of claim 19, wherein the pharmaceutical agent is hydrophilic, the solvent is aqueous, and the antisolvent is lipidic.

21. The method of claim 1, wherein the pharmaceutical agent is lipophilic, the solvent is lipophilic, and the antisolvent is hydrophilic.

22. The method of claim 12, wherein the solution is a lower layer having a first thickness and the antisolvent is an upper layer having a second thickness less than about 10% of the first thickness.

23. The method of claim 22, wherein the second thickness is in the range of about 0.1% to 5% of the first thickness.

24. The method of claim 22, wherein the upper layer is a molecular monolayer.

25. The method of claim 22, wherein the upper layer is a molecular bilayer.

26. The method of claim 1, wherein the size of the particle is in the range of approximately 0.1 nm to about 5 µm.

27. The method of claim 26, wherein the size of the particle is in the range of approximately 5 nm to about 2.5 µm.

28. The method of claim 1, wherein the pharmaceutical agent is selected from the group consisting of: analgesic agents; anesthetic agents; antiarthritic agents; respiratory drugs; anticancer agents; anticholinergics; anticonvulsants; antidepressants; antidiabetic agents; antidiarrheals; antihelminthics; antihistamines; antihyperlipidemic agents; antihypertensive agents; anti-infective agents; antiinflammatory agents; antimigraine preparations; antinauseants; antineoplastic agents; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations; central nervous system stimulants; cough and cold preparations; hormonolytics; hypnotics; hypoglycemic agents; immunosuppressive agents; leukotriene inhibitors; mitotic inhibitors; muscle relaxants; narcotic antagonists; nicotine; nutritional agents; ophthalmic drugs; parasympatholytics; psychostimulants; sedatives; steroids; sympathomimetics; tranquilizers; vasodilators; and combinations thereof.

29. The method of claim 1, wherein the pharmaceutical agent is a biomolecule selected from the group consisting of DNA, RNA, antisense oligonucleotides, peptides, proteins, ribosomes and enzyme cofactors.

30. The method of claim 29, wherein the pharmaceutical agent is DNA.

31. The method of claim 29, wherein the pharmaceutical agent is RNA.

32. The method of claim 29, wherein the pharmaceutical agent is an antisense oligonucleotide.

33. The method of claim 29, wherein the pharmaceutical agent is a peptide or protein.

34. The method of claim 29, wherein the pharmaceutical agent is a protein.

35. The method of claim 34, wherein the protein is a fluorescent protein.

36. The method of claim 29, wherein the pharmaceutical agent is a ribosome.

37. The method of claim 29, wherein the pharmaceutical agent is an enzyme cofactor.

38. The method of claim 29, wherein the pharmaceutical agent is a respiratory drug.

39. The method of claim 38, wherein the respiratory drug is selected from the group consisting of anti-inflammatory corticosteroids, bronchodilators, and mixtures thereof.

40. The method of claim 1, wherein the pharmaceutical agent is a diagnostic agent.

41. The method of claim 40, wherein the diagnostic agent is an MRI contrast agent.

42. The method of claim 41, wherein the diagnostic agent is a radio-labeled compound.

43. The method of claim 1, wherein the solution further comprises at least one pharmaceutical excipient.

44. The method of claim 1, wherein the solution further comprises a biodegradable polymer.

45. The method of claim 1, wherein the reservoir is adapted to contain no more than about 100 nanoliters of fluid.

46. The method of claim 45, wherein the reservoir is adapted to contain no more than about 10 nanoliters of fluid.

47. A method for generating a plurality of particles containing a pharmaceutical agent, the method comprising:
providing a plurality of reservoirs each containing a solution of the pharmaceutical agent in a solvent;
providing an antisolvent in a contained space in fluid communication with the solution in each reservoir, wherein the antisolvent is selected such that the pharmaceutical agent is less soluble in the antisolvent than in the solvent; and
applying focused acoustic energy to each reservoir so as to produce droplets of the solution into the antisolvent in the contained space, whereby admixture of the solution droplets and the antisolvent results in the precipitation of the pharmaceutical agent, forming solid particles.

48. The method of claim 47, wherein the focused acoustic energy is applied to each reservoir simultaneously using a plurality of acoustic ejection devices.

49. The method of claim 47, wherein the focused acoustic energy is applied to each reservoir in succession using a single acoustic ejection device.

50. A device for making solid particles of a pharmaceutical agent, comprising:
a reservoir containing a solution of the pharmaceutical agent in a solvent;
an antisolvent in a contained space in fluid communication with the solution in the reservoir such that droplets ejected from the solution are directed into the antisolvent, wherein the antisolvent is selected such that the pharmaceutical agent is less soluble in the antisolvent than in the solvent;
an acoustic ejector comprising an acoustic radiation generator for generating acoustic radiation and a focusing means for focusing the acoustic radiation at a focal point within the solution in the reservoir so as to eject a droplet therefrom; and
a means for positioning the ejector in acoustic coupling relationship to the reservoir.

51. The device of claim 50, comprising a single acoustic ejector.

52. The device of claim 50, comprising a plurality of acoustic ejectors positioned to direct focused acoustic energy to a plurality of loci within the solution so as to eject a plurality of droplets, whereby a plurality of solid particles is provided.

53. The device of claim 50, wherein the reservoir is adapted to contain no more than about 100 nanoliters of fluid.

54. The device of claim 50, wherein the reservoir is adapted to contain no more than about 10 nanoliters of fluid.

55. The device of claim 50, further comprising a means for maintaining the solvent in the reservoir at a constant temperature.

56. The device of claim 50, wherein the acoustic coupling relationship between the ejector and the solution in the reservoir is established by providing an acoustically conductive medium between the ejector and the reservoir.

57. The device of claim 50, wherein acoustic coupling between the ejector and the fluid in each reservoir is established at a predetermined distance between the ejector and each reservoir.

58. The device of claim 50, wherein the solvent is aqueous.

59. The device of claim 50, wherein the solvent is non-aqueous.

60. The device of claim 59, wherein the solvent is organic.

61. The device of claim 50, wherein the solvent is a supercritical fluid.

62. The device of claim 50, wherein the antisolvent is a supercritical fluid.

63. The device of claim 59, wherein the antisolvent is a supercritical fluid.

64. The device of claim 60, wherein the antisolvent is a supercritical fluid.

65. The device of claim 50, wherein the antisolvent is gaseous.

66. The device of claim 50, wherein the solution and the antisolvent are both present in the reservoir.

67. The device of claim 66, wherein a third fluid is present as a segregating layer between the solution and the antisolvent.

68. The device of claim 66, wherein the solvent and antisolvent are maintained in a substantially segregated state by maintaining the solvent, the antisolvent, or both, at a predetermined temperature and pressure.

69. The device of any one of claims 62, 63, 64, 66, 67 and 68, wherein the antisolvent is selected from the group consisting of carbon dioxide, water, ammonia, nitrogen, nitrous oxide, methane, ethane, ethylene, propane, butane, n-pentane, benzene, methanol, ethanol, isopropanol, isobutanol, monofluoromethane, trifluoromethane, chlorotrifluoromethane, monofluoromethane, hexafluoroethane, 1,1-difluoroethylene, 1,2-difluoroethylene, toluene, pyridine, cyclohexane, m-cresol, decalin, cyclohexanol, o-xylene, tetralin, aniline, acetylene, chlorotrifluorosilane, xenon, sulfur hexafluoride, propane, and combinations thereof.

70. The device of claim 69, wherein the antisolvent is carbon dioxide.

71. The device of claim 50, wherein the solution is a saturated solution.

72. The device of claim 50, wherein the pharmaceutical agent is hydrophilic, the solvent is hydrophilic, and the antisolvent is lipophilic.

73. The device of claim 72, wherein the pharmaceutical agent is hydrophilic, the solvent is aqueous, and the antisolvent is lipidic.

74. The device of claim 50, wherein the pharmaceutical agent is lipophilic, the solvent is lipophilic, and the antisolvent is hydrophilic.

75. The device of claim 66, wherein the solution is a lower layer having a first thickness and the antisolvent is an upper layer having a second thickness less than about 10% of the first thickness.

76. The device of claim 75, wherein the second thickness is in the range of about 0.1% to 5% of the first thickness.

77. The device of claim 75, wherein the upper layer is a molecular monolayer.

78. The device of claim 75, wherein the upper layer is a molecular bilayer.

79. The device of claim 50, wherein the pharmaceutical agent is selected from the group consisting of: analgesic agents; anesthetic agents; antiarthritic agents; respiratory drugs; anticancer agents; anticholinergics; anticonvulsants; antidepressants; antidiabetic agents; antidiarrheals; antihelminthics; antihistamines; antihyperlipidemic agents; antihypertensive agents; anti-infective agents; antiinflammatory agents; antimigraine preparations; antinauseants; antineoplastic agents; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations; central nervous system stimulants; cough and cold preparations; hormonolytics; hypnotics; hypoglycemic agents; immunosuppressive agents; leukotriene inhibitors; mitotic inhibitors; muscle relaxants; narcotic antagonists; nicotine; nutritional agents; ophthalmic drugs; parasympatholytics; psychostimulants; sedatives; steroids; sympathomimetics; tranquilizers; vasodilators; and combinations thereof.

80. The device of claim 50, wherein the pharmaceutical agent is a biomolecule selected from the group consisting of DNA, RNA, antisense oligonucleotides, peptides, proteins, ribosomes and enzyme cofactors.

81. The device of claim 80, wherein the pharmaceutical agent is DNA.

82. The device of claim 80, wherein the pharmaceutical agent is RNA.

83. The device of claim 80, wherein the pharmaceutical agent is an antisense oligonucleotide.

84. The device of claim 80, wherein the pharmaceutical agent is a peptide or protein.

85. The device of claim 80, wherein the pharmaceutical agent is a protein.

86. The device of claim 85, wherein the protein is a fluorescent protein.

87. The device of claim 80, wherein the pharmaceutical agent is a ribosome.

88. The device of claim 80, wherein the pharmaceutical agent is an enzyme cofactor.

89. The device of claim 80, wherein the pharmaceutical agent is a respiratory drug.

90. The device of claim 89, wherein the respiratory drug is selected from the group consisting of anti-inflammatory corticosteroids, bronchodilators, and mixtures thereof.

91. The device of claim 80, wherein the pharmaceutical agent is a diagnostic agent.

92. The device of claim 50, wherein the diagnostic agent is an MRI contrast agent.

93. The device of claim 50, wherein the diagnostic agent is a radio-labeled compound.

94. The device of claim 50, wherein the solution further comprises at least one pharmaceutical excipient.

95. The device of claim 50, wherein the solution further comprises a biodegradable polymer.

96. A device for making solid particles of a pharmaceutical agent, comprising:
   a plurality of reservoirs each containing a solution of the pharmaceutical agent in a solvent;
   an antisolvent in a contained space above and in fluid communication with the solution in each reservoir such that droplets ejected from the solution are directed into the antisolvent, wherein the antisolvent is selected such that the pharmaceutical agent is less soluble therein than in the solvent;
   an acoustic ejector comprising an acoustic radiation generator for generating acoustic radiation and a focusing means for focusing the acoustic radiation at a focal point within the solution in the reservoir so as to eject a droplet therefrom; and a means for positioning the ejector in acoustic coupling relationship to the reservoir.

97. The device of claim 96, comprising a single acoustic ejector.

98. The device of claim 96, comprising a plurality of acoustic ejectors positioned to direct focused acoustic energy to each reservoir so as to eject a plurality of droplets therefrom.

99. The device of claim 96, wherein each of the reservoirs is removable from the device.

100. The device of claim 96, wherein the reservoirs are individual wells in a well plate.

101. The device of claim 96, wherein the reservoirs are substantially acoustically indistinguishable.

102. The device of claim 96, comprising at least about 10,000 reservoirs.

103. The device of claim 102, comprising at least about 100,000 reservoirs.

104. The device of claim 103, comprising in the range of about 100,000 to about 4,000,000 reservoirs.

105. The device of claim 96, wherein each reservoir is adapted to contain no more than about 100 nanoliters of fluid.

106. The device of claim 96, wherein each reservoir is adapted to contain no more than about 10 nanoliters of fluid.

107. The device of claim 96, further comprising means for maintaining the solvent in each reservoir at a constant temperature.

108. The device of claim 96, wherein the acoustic coupling relationship between the ejector and the fluid in each reservoir is established by providing an acoustically conductive medium between the ejector and each reservoir.

109. The device of claim 96, wherein acoustic coupling between the ejector and the fluid in each reservoir is established at a predetermined distance between the ejector and each reservoir.

* * * * *